United States Patent
Bournay et al.

(10) Patent No.: US 7,138,536 B2
(45) Date of Patent: Nov. 21, 2006

(54) PROCESS FOR PRODUCING FATTY ACID ALKYL ESTERS AND GLYCEROL OF HIGH-PURITY

(75) Inventors: Laurent Bournay, Chaussan (FR); Arnaud Baudot, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/178,605

(22) Filed: Jul. 12, 2005

(65) Prior Publication Data

US 2006/0014974 A1    Jan. 19, 2006

(30) Foreign Application Priority Data

Jul. 12, 2004    (FR) .................................. 04 07777

(51) Int. Cl.
*C11C 1/00* (2006.01)
(52) U.S. Cl. ...................................... 554/167
(58) Field of Classification Search ............... 554/167
See application file for complete search history.

(56) References Cited

U.S. PATENT DOCUMENTS

| 2002/0013486 A1 | 1/2002 | Ergun et al. |
| 2004/0034244 A1 | 2/2004 | Bournay et al. |

FOREIGN PATENT DOCUMENTS

| EP | 1352893 A | 10/2003 |
| WO | WO 99/26913 A | 6/1999 |

*Primary Examiner*—Deborah D. Carr
(74) *Attorney, Agent, or Firm*—Millen, White, Zelano & Branigan, P.C.

(57) ABSTRACT

In a process for producing fatty acid alkyl esters and glycerol comprising
   at least one reaction stage in which a charge comprising a vegetable and/or animal oil and an alcohol are brought into contact, in the presence of a heterogeneous catalyst, so as to obtain an effluent comprising at least alkyl esters, glycerol and alcohol,
   and at least one separation stage during which a separation is carried out of at least one portion of the effluent so as to separate an alcohol-rich effluent and an alkyl esters-rich effluent,
at least one separation stage consists of a membrane separation using at least one alcohol-permeable membrane.

20 Claims, 5 Drawing Sheets

PROCESS FOR PRODUCING FATTY ACID ALKYL ESTERS AND GLYCEROL OF HIGH-PURITY

FIELD OF THE INVENTION

The invention relates to the field of processes for producing fatty acid alkyl esters and glycerol by bringing a vegetable and/or animal oil and an aliphatic alcohol into contact, in the presence of a heterogeneous catalyst.

PRIOR ART

The use of vegetable oil methyl esters (VOMEs) as substitute fuels for gasoil is destined to expand greatly over the next two decades. In fact, the presence in this product of monoglycerides in the form of traces (0.8% by mass maximum according to the standard in force), makes it possible to compensate advantageously for the loss of lubricant power due in particular to the reduction in the sulphur content of the gasoil. In Europe the sulphur content will be set at 50 ppm by mass in 2005 and 10 ppm by mass in 2008.

Moreover, the European Commission has adopted an action plan and two proposals for directives with a view to encouraging the use of substitute fuels in the transport sector, starting with regulatory and fiscal measures intended to promote biofuels. The action plan defines a strategy making it possible to replace 20% of diesel fuel and gasoline with substitute fuels in the road transport sector between now and 2020. One of the proposed directives stipulates that a minimum proportion of all fuels sold as from 2005 shall be biofuels. This proportion would be 2% initially and would reach 5.75% in 2010.

The production of vegetable oil methyl esters or biodiesel, essentially from rape-seed oil, exceeds 300,000 t/a in France. Moreover, other possible uses of these products exist, such as ecological solvents, and base compounds for the production of fatty alcohol sulphonates, amides, dimers of esters etc.

European patent application EP-A-1 352 893 describes a process comprising the implementation of an esterification reaction of a vegetable oil or an oil of animal origin using an aliphatic monoalcohol used in excess, with separation and recycling of the excess aliphatic monoalcohol, in order to produce glycerol and alkyl ester, in the presence of a heterogeneous catalyst.

Due to the very polar nature of methanol, its vaporization enthalpy is relatively high, approximately 1200 kJ/kg at ambient temperature and 610 kJ/kg at 200° C., and consequently its extraction from the reaction medium by vaporization requires a high energy consumption. Moreover, in order to be recycled into the reaction medium, this methanol must be condensed in order to then be compressed in liquid form via a pump.

SUMMARY OF THE INVENTION

An object of the invention is to supply a much more economical process making it possible, in particular, to remedy, at least partially, the prohibitive energy consumption of a stage of separation by vaporization.

A process has been found for producing fatty acid alkyl esters and glycerol using one or more transesterification reactions between a vegetable oil and an alcohol, in which an alcohol-rich effluent is separated from an alkyl esters-rich effluent via a membrane-type separation.

The transesterification reactions used in the present invention generally comprise:
  reaction of the oil, triglyceride, with an alcohol molecule in order to produce an ester molecule and a diglyceride;
  reaction of the diglyceride with an alcohol molecule in order to produce an ester molecule and a monoglyceride; and
  reaction of the monoglyceride with an alcohol molecule in order to produce an ester molecule and a glycerol molecule.

These reactions are generally balanced and can take place in parallel throughout the implementation of the process of the invention.

The membranes used in the membrane separation stage of the process of the invention are permeable to alcohol, the latter generally being recycled into the reaction medium. These membranes can moreover also be permeable to glycerol.

In a preferred version of the invention, the process comprises two reaction stages, each of these reaction stages being followed by at least one membrane separation stage.

DETAILED DESCRIPTION OF THE INVENTION

The present invention thus provides a process for producing fatty acid alkyl esters and glycerol which comprises:
  at least one reaction stage in which a charge comprising a vegetable and/or animal oil and an alcohol are brought into contact, in the presence of a heterogeneous catalyst, so as to obtain an effluent comprising at least alkyl esters, glycerol and alcohol,
  and at least one separation stage during which a separation of at least one portion of the effluent is carried out so as to separate an alcohol-rich effluent and an alkyl esters-rich effluent,
  said process being characterized in that at least one separation stage consists of a membrane separation using at least one alcohol-permeable membrane.

By fatty acid alkyl ester is meant an ester from the esterification of an aliphatic alcohol, in general saturated, on a carboxylic acid from a glyceride of vegetable or animal origin.

By glycerol is meant the tri-alcohol molecule having three carbon atoms, the chemical formula of which is $C_3H_8O_3$. The glycerol according to the invention can also be found in the form of glycerine. Glycerine can be defined as being a mixture comprising at least 50% by weight of glycerol as well as water, methanol, salts, organic matter without glycerol.

The vegetable and/or animal oils which can be used in the process of the invention can be any oil known to a person skilled in the art, for example rape-seed, palm, sunflower, soya bean, coconut, castor oil, as well as oils of animal origin such as suet.

The alcohol used in the process of the invention is generally an aliphatic alcohol. The alcohol of the process of the invention is most often an aliphatic monoalcohol. Preferably, the alcohol is essentially constituted by methanol and/or ethanol.

The improvement to the process of the invention essentially relates to the fact that it implements a separation stage comprising a membrane separation using at least one alcohol-permeable membrane.

Among the membrane separation technologies based on a selective transport of alcohol, such as methanol, through a film via a sorption-diffusion mechanism, those using a vapor permeation or a pervaporation can be envisaged.

The technologies based on vapor permeation are generally separations carried out on a gaseous-phase charge and based on the selective permeation of a fraction of the compounds of said charge, called the permeate, through a dense film. The phenomena involved are generally a sorption and a diffusion induced via a difference in chemical potential.

The technologies based on pervaporation are generally separations carried out on a charge in liquid phase. Pervaporation is based on a selective permeation of a fraction of the compounds of said charge, called the permeate, through a membrane essentially constituted by a dense film, said permeation being associated with a vaporization of this permeate downstream of the membrane. The vaporization is generally carried out either via a scavenging of the compartment downstream of the membrane using an inert gas, or via a partial evacuation of this compartment downstream of the membrane. In the same way as for vapor permeation, the phenomena involved are generally a sorption and a diffusion induced via a difference in chemical potential.

The saving in terms of energy consumption of these two technologies is, however, limited as they require either a total vaporization of the charge in the case of vapor permeation, or a vaporization of a large quantity of the alcohol in the form of permeate in the case of pervaporation.

It is generally preferred to use membrane separation techniques exploiting the reserve of mechanical pressure contained in the effluent leaving the reactor, with the aim of carrying out a hyperbaric filtration operation allowing a selective permeation of the methanol alone, or of the methanol and glycerol, through a membrane.

Preferably, the process of the invention comprises at least one membrane separation by nanofiltration and/or by reverse osmosis.

These membrane filtration techniques are particularly well suited to the separation of compounds having a small size from more bulky compounds, for example the separation of the methanol from a mixture of glycerol, esters and glycerides, or the separation of a mixture of methanol and glycerol from a mixture of esters and glycerides.

Nanofiltration membranes generally have an effective pore size ranging from 5 to 50 angstroms, whereas reverse osmosis membranes have an effective pore size of less than 10 angstroms.

Nanofiltration and reverse osmosis are generally based on a steric segregation mechanism associated with chemical affinity effects. The flow of the species crossing the selective layer of the membrane is principally convective in nature and this flow can be induced by a difference in mechanical pressure between the upstream and downstream faces of the membrane.

The compounds crossing the membrane (called "the permeate") are generally recovered in a low-pressure compartment, downstream of the membrane, whereas the "retentate", i.e. all of the compounds not crossing the membrane, is generally held in a high-pressure compartment upstream of the membrane.

In the process of the invention, membrane filtration has numerous advantages, such as:

the maintenance of the reactor effluent under pressure during the extraction of the alcohol and the reduction in the costs which were associated with the vaporization and condensation of the alcohol, the latter being, in the case of the invention, directly recovered in liquid phase downstream of the membrane.

Thus, while a second reaction stage is necessary in order to optimize the conversion into oil, there is a reduction in costs due to the maintenance under pressure of the alkyl esters-rich effluent which is retained upstream of the membrane of the membrane separation stage between the first and second reaction stages.

The pressure upstream of the membrane can be maintained at 1 to 12 MPa, preferably 2 to 8 MPa, more preferably 4 to 6 MPa. The pressure downstream can, for its part, range from 0.1 to 3.5 MPa, preferably from 0.1 to 2 MPa, and more preferably from 0.1 to 0.5 MPa.

According to an embodiment of the invention the membrane(s) used in the separation stage is (are) at least partially permeable to glycerol.

Preferably, at least one membrane comprises at least one polymer-based film. Numerous commercial models are available and are likely to be suitable for the envisaged application, due to their high chemical resistance in solvent medium.

Table 1 below shows a non-exhaustive list of the types of commercial membranes which may be suitable for the membrane separation of the invention.

TABLE 1

| Manufacturer | Commercial model | Nature of the selective layer | Technology |
|---|---|---|---|
| Celgard[1] | N30F | Polyethersulphone | NF |
| | NF-PES-10 | Polyethersulphone | NF |
| Koch Membrane Systems, Inc[2] | MPF 44 | Silicone | NF |
| | MPF 50 | Silicone | NF |
| Toray[3] | UTC 60 | PA | NF |
| | UTC 70 | PA | NF |
| Nitto[4] | NTR 729HF | PVA/PA | Low-pressure RO |
| | LFL 10 | PVA/PA | Low-pressure RO |
| | ES 10C | PVA/PA | Low-pressure RO |
| MET[5] (Grace Davison) | STARMEM 120 | Polyimide | NF |
| | STARMEM 122 | Polyimide | NF |
| | STARMEM 228 | Polyimide | NF |

NF = nanofiltration,
RO = reverse osmosis,
PVA = polyvinyl alcohol,
PA = polyamide
[1]Celgard Inc. 13800 South Lakes Drive Charlotte, NC 28273, U.S.A.
[2]Koch Membrane Systems, Inc. 850 Main Street Wilmington, MA U.S.A.
[3]Toray Membrane Products Dept. Head Office Toray Building, 8-1, Mihama 1 - chome, Urayasu, Chiba 279-8555, Japan
[4]Nitto Europe NV, Elkelaarstraat 22, Ind. Park Zuid, Zone 12A, 3600 Genk, Belgium
[5]Membrane Extraction Technol. Ltd, Dept Chem. Eng., Imperial College, London SW7 2BY, United Kingdom Among these polymer-based membranes, use of the following is preferred, in order of preference:
STARMEM 120 from MET (Grace Davison)
NF-PES-10 from Celgard and
UTC 60 from Toray.

In the case of a polymer membrane, it is recommended to carry out the membrane separation:
at a temperature generally above ambient temperature, and below 100° C., preferably below 80° C., more preferably at a temperature ranging from 40 to 65° C.,
at a retentate pressure below 15 MPa, preferably below 7 MPa, and
at a permeate pressure comprised between that of the retentate and the boiling pressure of the permeate at the temperature of the module, i.e. often below 0.5 MPa.

In a preferred way, the membrane comprises a polymer-containing film having undergone a physical treatment (by cooking or UV ray treatment for example) or a chemical treatment by reticulation. The mechanism of reticulation consists in creating chemical bridges between the polymer chains constituting the selective layer of the membrane. This treatment of reticulation leads to two technological improvements on the polymer-containing membranes.

Indeed, the reticulation significantly reduces the phenomena of swelling of the polymeric matrix constituting the selective layer of the membrane, induced by the organic compounds passing through said membrane. On the one hand, the screening effect of the polymeric film is thus strengthened, which results in an increase in the selectivity of the membrane having undergone the treatment of reticulation. In addition, the reduction of swelling has as a consequence a better chemical resistance of the membrane and thus an increase in its lifespan.

Preferably, the process of the invention uses at least one inorganic membrane. Although currently at the development stage and not yet offering the selectivities achieved by polymer membranes, these materials offer certain technological advantages compared with polymer membranes: better temperature resistance, longer life.

By way of non-exhaustive examples, the selective layer of these membranes can be constituted by the following materials:
alumina (Van Gestel T., Vandecasteele C., Buekenhoudt A., Dotremont C., Luyten J., Van der Bruggen B., Maesc G., "Corrosion Properties of Alumina and Titania NF Membranes", Journal of Membrane Science 214 (2003) 21–29),
titanium oxide (I. Voigt, G. Fischer, P. Puhlfürβ, M. Schleifenheimer, M. Stahn, "$TiO_2$—NF-Membranes on Capillary Supports", Separation and Purification Technology 32 (2003) 87–91; S. Benfer, U. Popp, H. Richter, C. Siewert, G. Tomandl, "Development and Characterization of Ceramic Nanofiltration Membranes", Separation and Purification Technology 22–23 (2001), 231–237),
amorphous silica, mesoporous silica (MCM-type), silica+zirconia (T. Tsuru, M. Miyawaki, H. Kondo, T. Yoshioka, M. Asaeda, "Inorganic Porous Membranes for Nanofiltration of Non-aqueous Solutions", Separation and Purification Technology 32 (2003) 105–109),
zirconia (S. Benfer, U. Popp, H. Richter, C. Siewert, G. Tomand, "Development and Characterization of Ceramic Nanofiltration Membranes", Separation and Purification Technology 22–23 (2001), 231–237),
alumina+titanium oxide (Van Gestel T., Vandecasteele C., Buekenhoudt A., Dotremont C., Luyten J., Van der Bruggen B., Maesc G., "Surface Modification of Alpha-$Al_2O_3$/$TiO_2$ Multilayer Membranes for Applications in Non-polar Organic Solvents", Journal of Membrane Science 224 (2003) 3–10).

It is to be noted that, as all these phases are polar in nature, the transfer of alcohol will be favoured compared with the more apolar compounds (such as the esters or the triglycerides) due to a better wettability of the alcohol in the pores of the selective layer.

In the case of an inorganic membrane, it is recommended to carry out the membrane separation at a temperature generally above ambient temperature, and below 200° C., preferably below 150° C., more preferably at a temperature ranging from 40 to 65° C.

According to an embodiment of the invention, the alcohol-rich effluent from the membrane separation stage can be recycled to the inlet of the reaction stage. This recycling can advantageously include the temporary storage of the alcohol in a buffer vessel.

Preferably, the alcohol-rich effluent from the membrane separation stage can undergo a purification stage before being recycled to the inlet of the reaction stage. This purification stage can comprise one or more separation operations, among which there can be mentioned a dehydration of the alcohol, optionally a separation of the glycerol from the alcohol or any other separation known to a person skilled in the art. This separation has the advantage of extracting any compound contaminating the alcohol which could inhibit or slow down the transesterification reaction or reduce its yield.

According to another embodiment, the alkyl esters-rich effluent can be sent to a stage of separation of the alcohol, for example by vaporization under vacuum, which makes it possible to extract the traces of alcohol. The thus-separated alcohol is advantageously recycled to the inlet of the reaction stage. In a first case, the alcohol from this separation stage can be recycled directly to the inlet of the reaction stage, optionally via a buffer vessel. In a second case, the alcohol from this separation stage can also, before being recycled to the inlet of the reaction stage, undergo a purification stage which can include one or more separation operations, among which there can be mentioned a dehydration of the alcohol, optionally a separation of the glycerol from the alcohol or any other separation known to a person skilled in the art. This last separation has the advantage of extracting any compound contaminating the alcohol which could inhibit or slow down the transesterification reaction or reduce its yield.

According to a version of the process of the invention, the calories of the effluent from the reaction stage are used to reheat the charge of said reaction stage.

The separation stage is preferably carried out such that the alkyl esters-rich effluent has an alcohol content comprised between 0.1 and 25% by weight.

According to another version of the process of the invention, at least a first and a second reaction stage are implemented, each of these reaction stages being followed by at least one membrane separation stage. Preferably, the conversion of the oil in the first reaction stage is at least 90% by weight. The second reaction stage is preferably implemented such that the monoglycerides content of the effluent from said stage is less than or equal to 0.8% by weight.

DETAILED DESCRIPTION OF THE FIGURES

For better understanding, several embodiments of the device of the invention are illustrated by FIGS. 1 to 7. These embodiments are given by way of examples and are not limitative in character. These illustrations of the device of the invention do not comprise all of the components necessary for its implementation. Only the elements necessary for understanding the invention are shown there, a person skilled in the art being capable of supplementing these representations in order to put the invention into practice.

Figure 1:
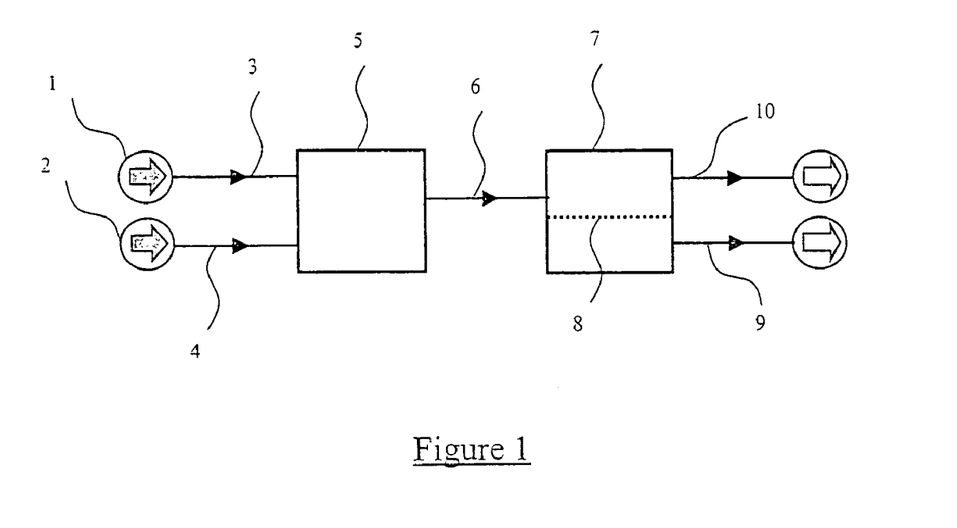
FIG. 1 represents, non-limitatively, a simplified embodiment of the process of the invention comprising a reaction stage and a membrane filtration stage.

FIG. 1 represents an embodiment of the process of the invention in which triglycerides 1 and alcohol 2 are respectively introduced via lines 3 and 4 into a transesterification reactor 5. The products of the reaction are removed via a line 6 at a pressure above the bubble pressure of these products and at a temperature below 250° C.

The products are then introduced into a membrane separation module 7 comprising a membrane 8 which is selectively permeable to alcohol. This membrane separation operation can, in this case, use a nanofiltration or reverse osmosis membrane, or a combination of these two technologies.

The alcohol is recovered in a line 9 and constitutes most of the permeate. The retentate, i.e. all of the compounds that have not passed through the membrane, chiefly comprises esters. This retentate is recovered via a line 10.

Figure 2:
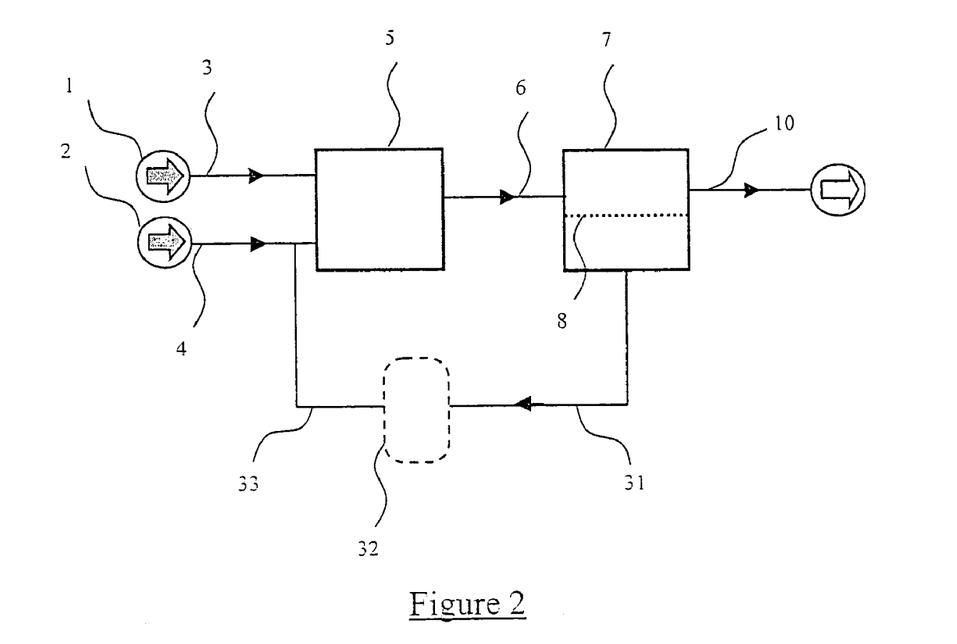
FIG. 2 represents, non-limitatively, an embodiment also comprising a recycling of the alcohol into the reaction stage.

FIG. 2 represents an embodiment of the process of the invention comprising most of the elements of FIG. 1 with, in addition, a recycling of the alcohol. In this case, the alcohol recovered after membrane separation is recycled, via a line 31, into a buffer vessel 32, before being sent, via a line 33, into the reactor.

Figure 3:
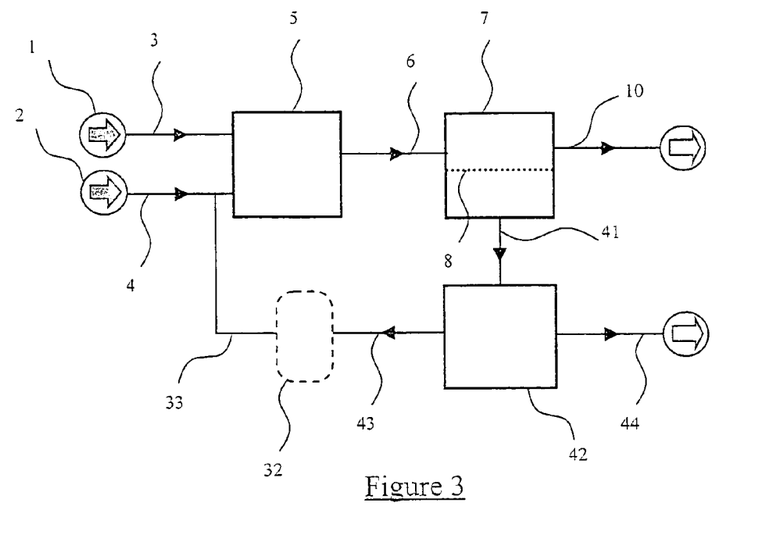
FIG. 3 represents, non-limitatively, an embodiment also comprising an additional stage of purification of the alcohol before the recycling of the latter.

FIG. 3 represents an embodiment of the process of the invention comprising most of the elements of FIG. 2 with, in addition, an extra alcohol purification stage. In this case, the alcohol is removed from the membrane separation stage via a line 41 in order to be sent into a separation stage 42. The thus-purified alcohol is sent, via a line 43, into the buffer vessel 32 before being sent, via a line 33, into the reactor. The contaminants are, for their part, removed via a line 44.

Figure 4:
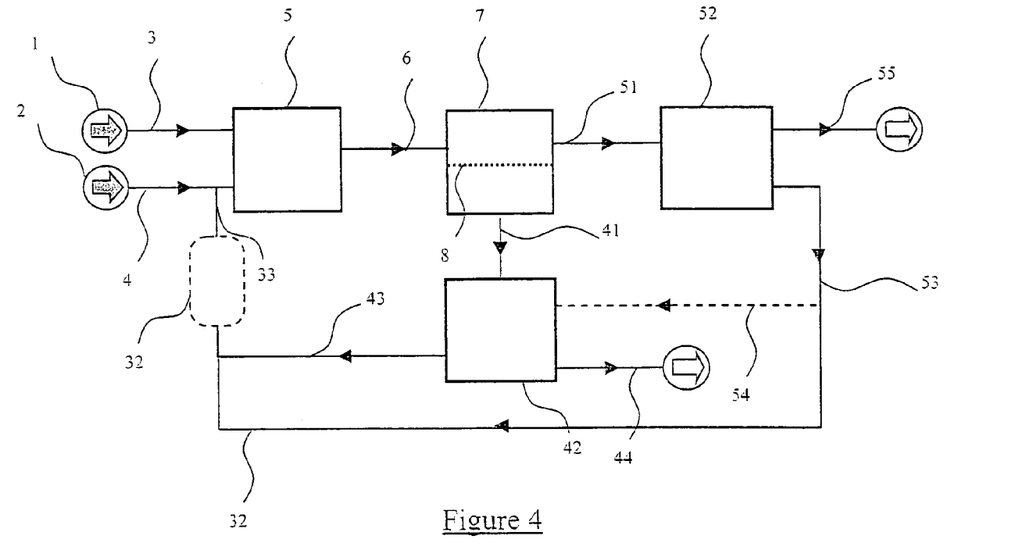
FIG. 4 represents, non-limitatively, an embodiment also comprising a stage of separation of the alcohol originating from the retentate.

FIG. 4 represents an embodiment of the process of the invention comprising most of the elements of FIG. 3 with, in addition, a stage of separation of the alcohol from the retentate. In this case, the retentate, which chiefly comprises esters but also alcohol, is sent, via a line 51, into a stage of separation of the alcohol 52, for example by vaporization under vacuum. The alcohol-rich flow from this separation stage 52 can be recycled, via a line 53, into the reactor via the buffer vessel 32 or via the separation stage 42 using a line 54. The esters-rich flow is, for its part, removed via a line 55.

Figure 5:
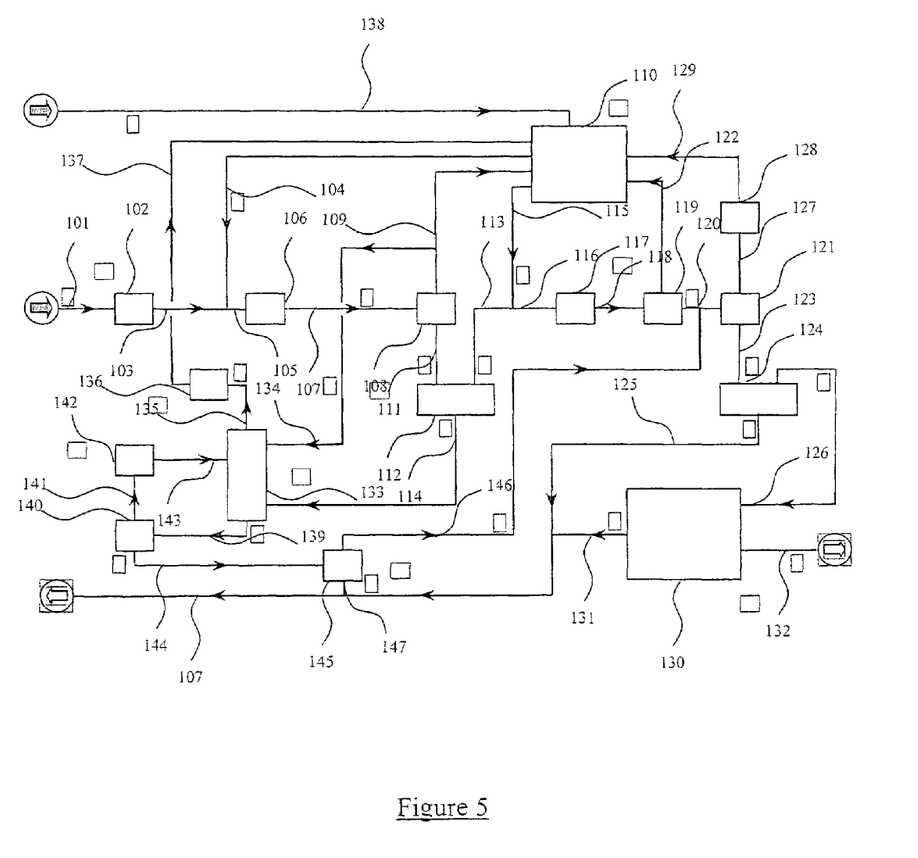
FIG. 5 represents, non-limitatively, a sequence for the industrial implementation of the process of the invention.

FIG. 5 represents a particular sequence for putting the process of the invention into practice.

The oil to be treated generally comes from a unit for crushing rape seeds, or seeds of other vegetable oils such as palm, sunflower, soya bean, coconut, castor oil, as well as oils of animal origin such as suet.

The crude rape seed oil is passed, via a line 101, into a vacuum dryer 102 so as to obtain a water content of less than 700 ppm by mass. The dried oil is sent, using a line 103, to be mixed with recycle methanol supplied via a line 104. The mixture obtained contains between 20% and 80% by weight, preferably between 45% and 55% by weight of oil.

This mixture is sent, via a line 105, successively into a pump (not shown) in order to be compressed to 6.2 MPa, into an exchanger (not shown) in order to be heated to 473 K, or 483 K at the end of the catalyst's life, and into a reactor 106. The reactor contains a fixed bed of a catalyst based on zinc aluminate in the form of extrudates. The hourly volume velocity within the reactor 106, i.e. the ratio of the hourly volume flow rate of oil to be treated to the volume of catalyst, can range from 0.1 to 1.2 h$^{-1}$, preferably from 0.4 to 0.6 h$^{-1}$. The conversion into oil achieved under these conditions is at least 90% by mass, generally at least 92% by mass.

On leaving the reactor 106, the effluent is removed via a line 107. This effluent comprises ester, glycerol, methanol and the little-converted or unconverted glycerides (oil, di- and monoglycerides). This effluent is then cooled by heat exchange with a process fluid before being heated, which allows a good heat integration of the process. In a standard fashion, a "charge-effluent" exchanger (not shown) is used around the reactor. In order to carry out this heat exchange, the reactor charge is pre-heated with its effluent, thus saving some of the heating energy. The reactor charge often requires additional heating in order to reach the reaction temperature. The effluent in the line 107 is then cooled to a temperature ranging from 293 to 423 K, preferably from 313 to 353 K.

The effluent is then sent, by the line 107, into a series of nanofiltration membrane modules 108, maintained at a pressure close to 6 MPa. This nanofiltration stage can be dimensioned such that the residual methanol content in the mixture is comprised between 5 and 25% by weight, preferably between 10 and 20% by weight. The methanol in liquid phase is recovered from the permeate, using a line 109, and is then recycled into a buffer vessel 110. The retentate, for its part, is cooled to 323 K and sent, via a line 111, into a settling vessel 112 in order to separate an ester-rich, upper phase, which is removed via a line 113, from a glycerol-rich lower phase, which is removed via a line 114.

The ester-rich phase removed from the settling vessel 112 via the line 113 is mixed with methanol taken from the buffer vessel 110 by the line 115 so as to obtain once again a mixture the ester content by mass of which is comprised between 20% and 80% by weight, preferably between 45% and 55% by weight. This mixture is passed via a line 116 upwards into a second reactor 117 identical to the first, and operating under operating conditions very close to those of the reactor 106. The operating conditions of these reactors 106 and 107 are generally practically identical, and the catalyst used in each of the reactors is generally the same. The conversion generally makes it possible to meet the fuel specification for monoglycerides in the ester, recovered in a line 118, which is generally 0.8% by weight maximum.

In the same way as for the first reaction stage, the effluent recovered in the line 118 is cooled in a charge-effluent exchanger (not shown) around the reactor 117. Thus, the charge of the reactor 117 can be pre-heated, additional heating generally being necessary in order to reach the reaction temperature.

The effluent is then sent, via the line 118, into a series of separation stages 119 comprising a nanofiltration stage, then via a line 120, to a separation-by-evaporation stage 121, in order to extract the methanol contained in the effluent from the reactor 117. The nanofiltration stage is carried out so as to deliver a retentate, i.e. a flow retained upstream of the membrane, the composition of which is similar to that obtained in stage 108, and the second separation-by-evaporation stage 121 is carried out under vacuum so as to obtain a liquid phase having a maximum of 500 ppm by mass of methanol, preferably 200 ppm by mass. This allows the drying of the ester to 200 ppm by mass of water maximum.

The methanol from the permeate of the nanofiltration stage 119 is recycled into the buffer vessel 110 via a line 122. The liquid effluent from the separation-by-evaporation stage 121 is sent, after cooling, via a line 123, into a settler 124, in which a very pure glycerine phase is obtained, sent to the limit of the unit via a removal line 125, and an ester phase, recovered via a line 126 and which undergoes a subsequent treatment which will be described hereafter. The methanol vapor from the evaporator 121 is sent, via a line 127, into a condenser 128, then recycled, via a line 129, into the buffer vessel 110.

The ester phase from the settler 124 is then treated so as to meet the fuel specification as regards the total glycerol (free and potential) content, which is 0.25% by weight maximum. This treatment of the crude ester can be carried out in different ways. In the present case, the ester is sent via the line 126 into a coalescer 130, in which the traces of free glycerol are eliminated. The ester can optionally then be sent onto the adsorbent masses of an adsorber, not shown, generally an ion-exchange resin, which fixes the dissolved glycerol. The glycerol, very pure, separated from the ester, is sent via a line 131 at the limit of the unit. The final ester, for its part, is recovered via a line 132. The treatment of the ester could be carried out, in other cases, using one or more stages of washing the ester with water.

The flow of glycerine from the buffer vessel 112, via the line 114, is generally treated so as to achieve a maximum methanol content of 5000 ppm by mass, and a maximum non-glycerine organics (MNGO) content of 1% by weight, which corresponds to the generally acceptable commercial level. The elimination of the methanol contained in the flow of glycerine is generally carried out in two stages. The first stage is generally carried out at the base of a distillation column 133, which makes it possible to obtain a glycerine at the base of the column having a methanol content of up to 5% by weight and to separate the water from the methanol on the trays at the top, the methanol at the top comprising 800 ppm by mass of water maximum, preferably 500 ppm. The column 133 is also supplied via a flow of methanol coming from the stage 108 via a line 134. The purified methanol leaving at the top of the column 133 is sent, via a line 135, into a condenser 136, before being sent, via a line 137, into the buffer vessel 110.

This operation is necessary in order to deconcentrate the water which enters the unit by the charge oil 101, the drying of which is limited to 500 ppm by mass. If it were necessary to take this drying stage further, it would be necessary either to increase the vacuum level, which is expensive, or increase the temperature, thus risking decomposition of some of the oil. The other water input can also come from the fresh methanol sent into the buffer vessel 110 via a line 138. Using the driest commercial methanol, i.e. grade A, it is possible to ensure a water content of less than 1000 ppm by mass. The water entering the system by these two routes accumulates in the methanol loop. The water is an inhibitor of the catalyst, and beyond a water content of 1000 ppm by mass in the reaction mixture the oil conversion drops appreciably.

The glycerine extracted from the base of the column 133, containing approximately 5% methanol, is sent via a line 139, into a vacuum evaporator 140. The methanol vapor is sent, via a line 141, into a condenser 142 and recycled, via a line 143, into the column 133. The glycerine flow extracted from the evaporator 140, containing approximately 3000 ppm of methanol, is sent, via a line 144, into a settling vessel 145. The ester phase from the top of the settling vessel 145 is sent, via a line 146, to the inlet of the evaporator 121 and the purified glycerol leaves at the limit of the unit, via the line 147.

As the transesterification reaction consumes some of the methanol, it is necessary to introduce fresh methanol, via the line 138. Some of this fresh methanol is sent into the methanol charge vessel, or buffer vessel 110, the other part being able to serve to regenerate the ion-exchange resins used in the ester treatment (not shown).

EXAMPLE 1

Not in Accordance with the Invention

In this example, the extraction of the excess alcohol at the outlet of the transesterification reactors is carried out by evaporation. The pressures are given in absolute values.

Figure 6:
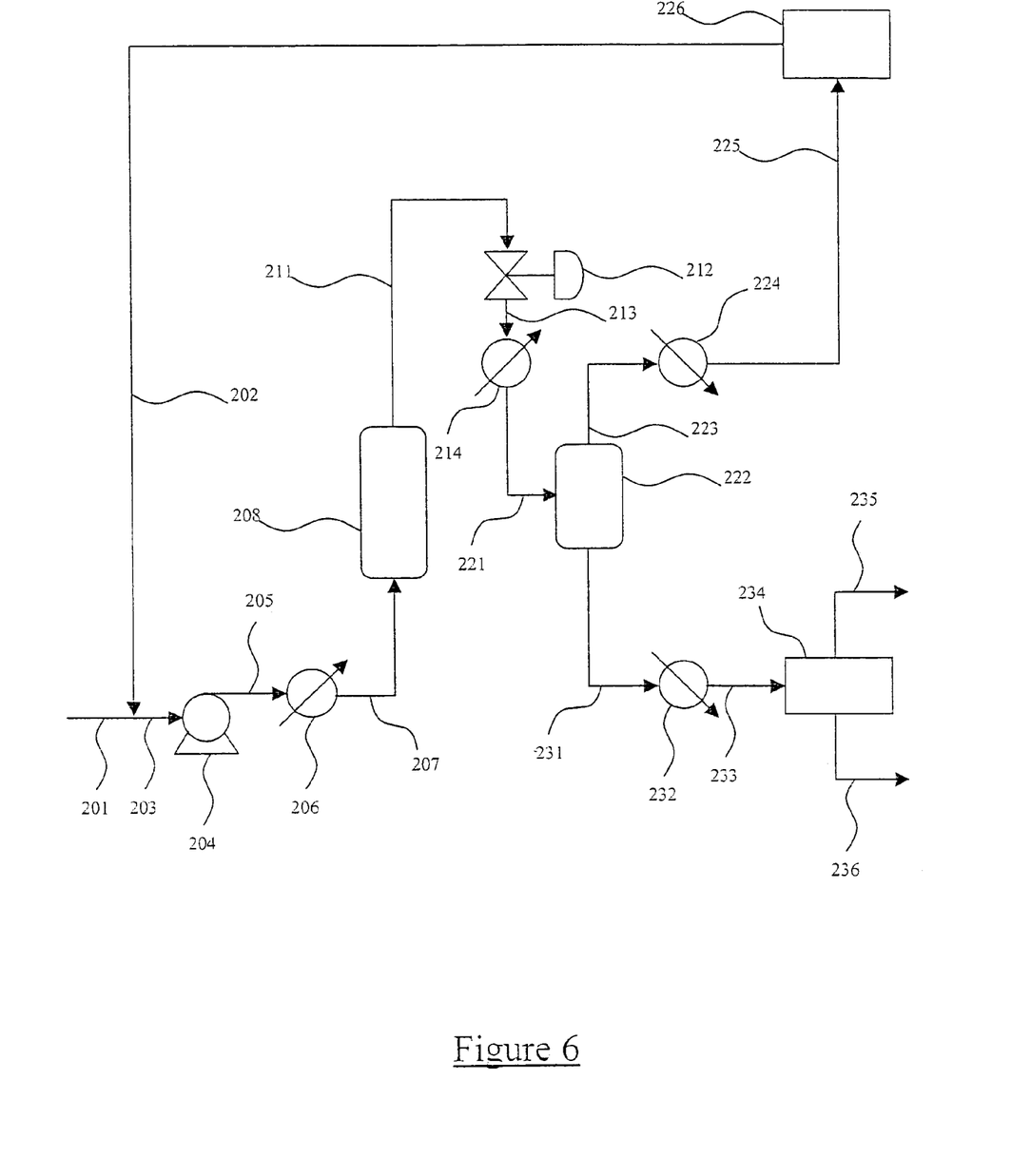
FIGS. 6 and 7 serve to illustrate respectively a first example not in accordance with the invention and a second example in accordance with the invention.

This example is based on a sequence according to the prior art shown in FIG. 6, i.e. not in accordance with the present invention.

The oil to be treated comes from a rape seed crushing unit. It would also be possible to treat other vegetable oils, such as palm, sunflower, soya bean, coconut, castor oil, as well as oils of animal origin such as suet. The crude rape seed oil was previously sent to a vacuum dryer in order to obtain a water content of less than 700 ppm by mass. In the remainder of the text, the term "dried oil" is used to refer to the charge oil that has undergone this treatment.

In the sequence of FIG. 6, the dried oil is fed via the line 201 in order to then be mixed with recycle methanol fed via a line 202, at a pressure of 0.25 MPa. The mixture containing the dried oil and the recycle methanol thus obtained comprises 50% by weight oil and has a temperature of 323 K. This mixture is sent, via a line 203, into a pump 204, in order to be compressed there to 6.2 MPa. The thus-compressed mixture is then sent, using a line 205, into a heat exchanger 206 in order to be heated there to 473 K. This temperature can reach 483 K at the end of the catalyst's life. The hot fluid from this heat exchange is high-pressure vapor, i.e. saturated vapor at 2.8 MPa, i.e. a temperature of 503 K. The vapor flow rate necessary in the exchanger 206 for this stage of heating the reagents is 1000 kg/h.

The thus-heated mixture is then sent via a line 207 upwards into a reactor 208 containing a fixed bed of a catalyst based on zinc aluminate in the form of extrudates. The hourly volume velocity (HVV), i.e. the ratio of the hourly volume flow rate of charge (oil+methanol) to be treated to the volume of catalyst, is 0.5 h$^{-1}$. On leaving the reactor 208, the effluent comprises ester, glycerol, methanol and the little-converted or unconverted glycerides (oil, di- and monoglycerides).

This effluent is then sent, using a line 211, through an expansion valve 212, in order to be expanded to a pressure close to 0.25 MPa. This expansion has the effect of vaporizing a large part of the methanol contained in the mixture. The thus-expanded effluent is then sent, via a line 213, into a vaporizer 214 which has the task of evaporating part of the methanol remaining in the liquid portion of the effluent. This heating stage is carried out by heat exchange with a flow rate of 77 kg per hour of low-pressure vapor, i.e. vapor saturated at 0.50 MPa, i.e. a temperature of 425 K. This evaporation stage is carried out in such a manner than the non-evaporated residual methanol content is 15% by weight.

The effluent is sent, using a line 221, into a flash buffer vessel 222, in which the methanol vapor is separated from the liquid. The methanol vapor is sent, via a line 223, then cooled and condensed at 323 K in a condenser 224, before being sent, via a line 225, to a buffer vessel 226. This stage of condensation and cooling of the liquid is carried out by heat exchange with a flow rate of 42526 kg/h of cooling water arriving at 30° C. and leaving at 40° C. The recycle methanol, which is mixed with the oil charge, is recycled from the buffer vessel 226 via the line 202.

The liquid from the flash vessel 222 is sent, using a line 231, into an exchanger 232, in order to be cooled there to 323 K. This stage of cooling the liquid is carried out by heat exchange with a flow rate of 7028 kg/h of cooling water arriving at 30° C. and leaving at 40° C. The liquid is then sent, using a line 233, into a settling vessel 234 in order to separate an ester-rich, upper phase feeding the second reaction section (not shown), using a line 235, from a glycerine-rich lower-phase, removed via a line 236.

EXAMPLE 2

According to the Invention

In this example, the extraction of the excess alcohol at the outlet of the transesterification reactors is carried out by membrane route. The pressures are given in absolute values.

Figure 7:
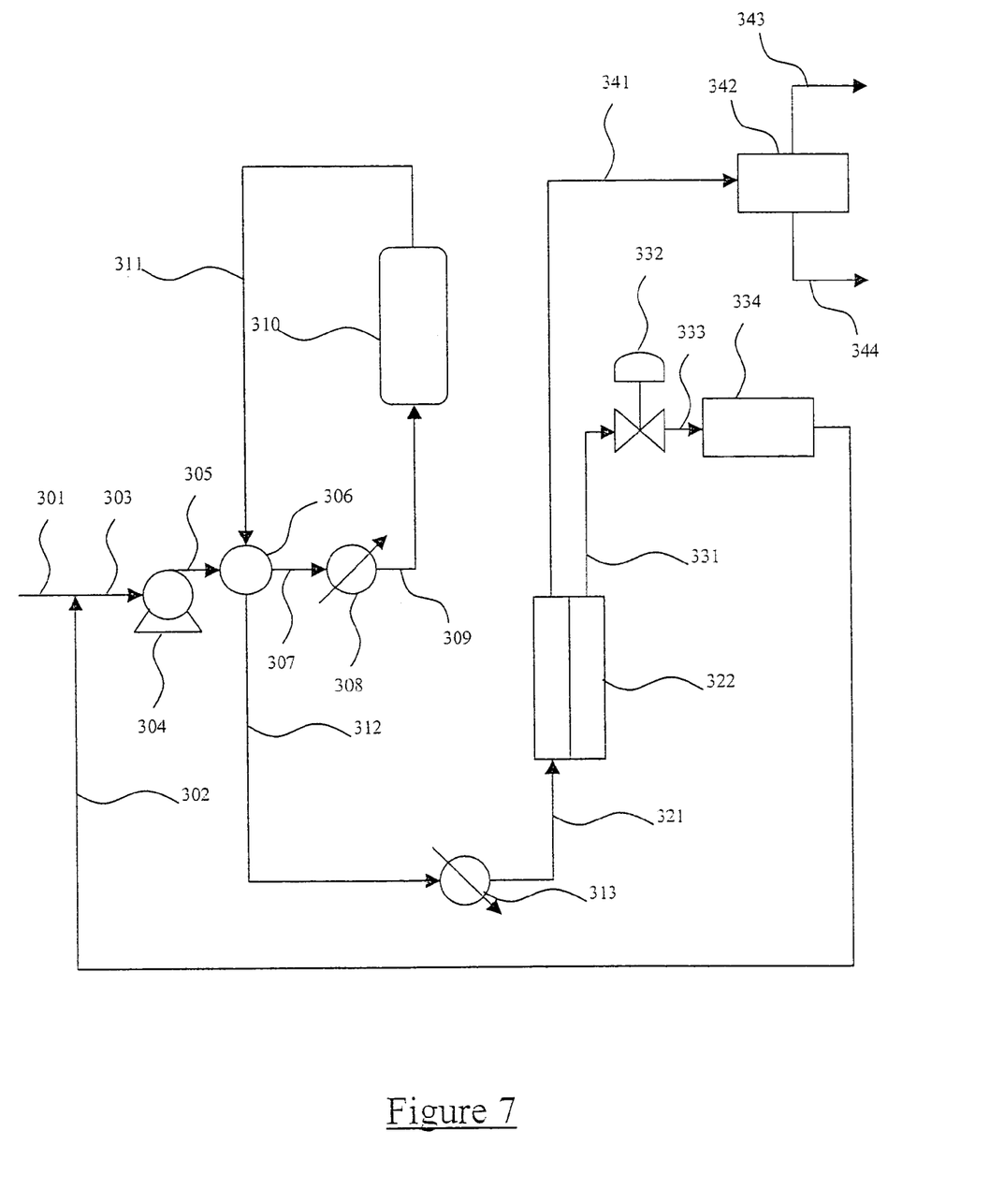

This example is based on a sequence according to the invention shown in FIG. 7, i.e. in accordance with the present invention.

As in the preceding case, the oil to be treated comes from a crushing unit. In the same way, the crude rape seed oil has undergone a vacuum drying so as to obtain a water content of less than 700 ppm by mass.

In the sequence of FIG. 7, the dried oil is fed via the line 301 in order to then be mixed with recycle methanol fed via a line 302, at a pressure of 0.25 MPa. The mixture of dried oil and recycle methanol comprises 50% by weight of oil and has a temperature of 323 K. This mixture is sent, via a line 303, into a pump 304, in order to be compressed there to 6.2 MPa. The thus-compressed mixture is then sent, using a line 305, into a heat exchanger 306 in order to be heated there to 473 K.

The exchanger 306 is an exchanger of the charge-effluent type which uses the calories of the effluent from the transesterification reactors in order to reheat the charge. Thus the reactor charge is preheated with its effluent, which makes it possible to save some of the heating and cooling energy.

The mixture is sent, via a line 307, into a heat exchanger 308 in order to be heated to 473 K (483 K at the end of the catalyst's life). The hot fluid from this heat exchange is high-pressure vapor, i.e. vapor saturated at 2.8 MPa, i.e. a temperature of 503 K. The vapor flow rate necessary in the exchanger 308 for this stage of heating the reagents is 492 kg/h.

The thus-heated mixture is then sent, via a line 309, upwards into a tubular reactor 310 containing a fixed bed of a catalyst based on zinc aluminate in the form of extrudates. The hourly volume velocity, HVV, i.e. the ratio of the hourly volume flow rate of charge to be treated to the volume of catalyst, is 0.5 $h^{-1}$. On leaving the reactor 310, the effluent comprises ester, glycerol, methanol and the little-converted or unconverted glycerides (oil, di- and monoglycerides).

This effluent is then sent via a line 311, into the charge-effluent exchanger 306 in order to be cooled a first time. The thus-cooled effluent is sent, via a line 312, into a cooler 313, in which it is cooled a second time to a temperature of 323 K. This stage of cooling the liquid is carried out by heat exchange with a flow rate of 23706 kg/h of cooling water arriving at 30° C. and leaving at 40° C.

The thus-cooled effluent is conveyed, using a line 321, into a series of nanofiltration membrane modules 322, maintained at a pressure close to 6 MPa (or 6 MPa upstream and 1 MPa downstream). This nanofiltration stage is dimensioned such that the residual methanol content in the effluent is 15% by weight. The membrane model used is the STARMEM 120 from MET (Grace Davison). The membrane modules are maintained at a temperature of 323 K. The charge flow rate at the inlet to the membrane modules is equal to 100 kg/h per $m^2$ of membrane installed.

The methanol recovered from the permeate in liquid phase is sent, via a line 331, through a pressure-control valve 332, before being sent via a line 333 to a buffer vessel 334. The recycle methanol, which is mixed with the oil charge, is recycled from the buffer vessel 334 via the line 302.

The liquid recovered from the other part of the nanofiltration membrane modules 322 is sent, using a line 341, into a settling vessel 342 in order to separate an ester-rich upper phase supplying the second reaction section (not shown), using a line 343, and a glycerine-rich lower phase removed via a line 344.

Table 2 below aims to summarize the water and water vapor consumption in the cases of Examples 1 and 2.

TABLE 2

|  | Example 1 | Example 2 |
|---|---|---|
| High-pressure vapor (kg/h) | 1000 | 493 |
| Low-pressure vapor (kg/h) | 77 | 0 |
| Cooling water (kg/h) | 49554 | 23706 |

In the diagrams of Examples 1 and 2, the performances in terms of treated oil capacity, conversion and quality of ester produced are the same. The results in Table 2 show that the use of membrane modules leads to a 50.7% reduction in the consumption of high-pressure vapor, a 52% reduction in the consumption of cooling water, and a complete elimination of the consumption of low-pressure vapor.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 04/07.777, filed Jul. 12, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. In a process for producing fatty acid alkyl esters and glycerol comprising:
   at least one reaction stage in which a charge comprising a vegetable and/or animal oil and an alcohol are brought into contact, in the presence of a heterogeneous catalyst, so as to obtain an effluent comprising at least alkyl esters, glycerol and alcohol,
   and at least one separation stage during which a separation of at least one portion of the effluent is carried out so as to separate an alcohol-rich effluent and an alkyl esters-rich effluent, the improvement wherein the at least one separation comprises passing at least one portion of the effluent through at least one alcohol-permeable membrane.

2. A process according to claim 1, wherein the alcohol comprises essentially methanol and/or ethanol.

3. A process according to claim 1 wherein the at least one membrane separation is carried out by nanofiltration.

4. A process according to claim 1 wherein the at least one membrane separation is carried out by reverse osmosis.

5. A process according to claim 1 wherein the alcohol comprises glycerol.

6. A process according to claim 1 wherein the least one membrane comprises a polymer-based film.

7. A process according to claim 1 wherein the membrane(s) is (are) inorganic.

8. A process according to claim 1 wherein the alcohol-rich effluent from the membrane separation stage is recycled to the inlet of the reaction stage.

9. A process according to claim 8, wherein the recycling includes the temporary storage of the alcohol in a buffer vessel.

10. A process according to claim 1 wherein the alcohol-rich effluent from the membrane separation stage undergoes a purification stage before being recycled to the inlet of the reaction stage.

11. A process according to claim 1 wherein the alkyl esters-rich effluent is sent into a further stage of separation of the alcohol.

12. A process according to claim 11, wherein the alcohol from the stage of separation of the alkyl esters-rich effluent is recycled to the inlet of the reaction stage.

13. A process according to claim 12, wherein the alcohol from the stage of separation of the alkyl esters-rich effluent undergoes a purification stage before being recycled to the inlet of the reaction stage.

14. A process according to claim 1 wherein the effluent from the reaction stage is passed in indirect heat exchange with the charge of said reaction stage.

15. A process according to claim 1 wherein the separation stage is carried out such that the alkyl esters-rich effluent has an alcohol content comprised between 0.1 and 25% by weight.

16. A process according to claim 1 comprising at least first and second reaction stage each of these reaction stages being followed by at least one membrane separation stage.

17. A process according to claim 16, wherein the conversion of said vegetable and/or animal oil in the first reaction stage is at least 90% by weight.

18. A process according to claim 16 wherein the monoglycerides content of the effluent from said second reaction stage is less than or equal to 0.8% by weight.

19. A process according to claim 1 wherein the alcohol comprises an aliphatic mono alcohol.

20. A process according to claim 1, wherein the alcohol comprises essentially methanol and/or ethanol.

* * * * *